(12) United States Patent
Anderson

(10) Patent No.: US 6,487,269 B2
(45) Date of Patent: Nov. 26, 2002

(54) APPARATUS FOR ANALYSING A SAMPLE

(75) Inventor: Robin John Anderson, Oxon (GB)

(73) Assignee: Oxford Instruments Analytical Limited, Oxon (GB)

( * ) Notice: Subject to any disclaimer, the term of this patent is extended or adjusted under 35 U.S.C. 154(b) by 0 days.

(21) Appl. No.: 09/984,654

(22) Filed: Oct. 30, 2001

(65) Prior Publication Data

US 2002/0054661 A1 May 9, 2002

(30) Foreign Application Priority Data

Nov. 9, 2000 (GB) .............................................. 0027429

(51) Int. Cl.⁷ ................................................ G01T 1/36
(52) U.S. Cl. .......................... 378/44; 356/327; 250/393
(58) Field of Search ............................. 378/44, 45, 46; 353/20; 250/358.1, 393; 356/327, 366

(56) References Cited

U.S. PATENT DOCUMENTS

| 3,919,548 A | | 11/1975 | Porter | 250/277 |
| 3,944,822 A | | 3/1976 | Dzubay | 250/272 |
| 4,048,496 A | * | 9/1977 | Albert | 250/272 |
| 4,647,207 A | * | 3/1987 | Bjork et al. | 356/364 |
| 5,220,591 A | * | 6/1993 | Ohsugi et al. | 378/45 |
| 5,754,620 A | * | 5/1998 | Hossain et al. | 378/45 |
| 6,041,095 A | | 3/2000 | Yokhin | 378/45 |
| 6,226,347 B1 | * | 5/2001 | Golenhofen | 378/45 |
| 6,269,142 B1 | * | 7/2001 | Smith | 378/57 |

OTHER PUBLICATIONS

Richard W. Ryan et al., Polarized Beam X–ray Fluorescence, pp. 491–510.
Birgit Kanngieber et al., The Comparison of Three Excitation Modes in the Energy Dispersive X–ray Fluorescence Analysis, pp. 1001–1007.
I.G. Grigorieva et al., HOPG as a Powerful X–Ray Optics, pp. 115–119.

* cited by examiner

Primary Examiner—Robert H. Kim
Assistant Examiner—Irakli Kiknadze

(57) ABSTRACT

Apparatus for analysing a sample comprises:
a. A radiation source for generating a radiation beam;
b. A sample holder for holding the sample in use;
c. A polariser for polarising the radiation beam;
d. A radiation beam selector for selectively exposing the sample to either the radiation beam or the polarised radiation beam; and,
e. A detector for detecting radiation emitted by the sample.

10 Claims, 3 Drawing Sheets

APPARATUS FOR ANALYSING A SAMPLE

FIELD OF THE INVENTION

The present invention relates to apparatus for analysing a sample and in particular to apparatus for performing energy dispersive X-ray fluorescence.

DESCRIPTION OF THE PRIOR ART

Energy Dispersive X-ray Fluorescence (EDXRF) is a powerful analytical technique that is capable of simultaneous analysis of a wide range of elements in a variety of different sample types.

EDXRF uses an X-ray spectrometer which includes an X-ray tube for generating primary X-rays which are used to expose a sample material. The spectral output from the X-ray tube usually consists of characteristic X-ray lines of the anode material superimposed on a background continuum. The sample emits fluorescence radiation characteristic of the materials within the sample and an X-ray detector is then used to detect this radiation.

However, the detector, with its associated electronics, has to process the entire X-ray spectrum emitted from the sample and the measurement efficiency decreases with increasing count rate. The primary X-rays incident on the sample material can be scattered from the sample so as to also impinge on the detector. These scattered X-rays then contribute to the overall count rate detected by the detector, thereby reducing the measurement efficiency and thus the precision of the measured readings of the sample composition. This is especially true for low atomic number samples such as organic materials or oxides where the matrix will very efficiently scatter radiation. In most cases it is possible to reach the count rate limit of state-of-the-art processing electronics using only modest power levels from conventional X-ray tubes.

When using this direct excitation technique, it is possible to remove much of the background continuum by placing a suitable absorption filter between X-ray tube and sample to improve the quality of the primary excitation. This is usually the most efficient excitation method for the analysis of major and minor concentration levels. However, at trace levels the elements of interest may represent only a small proportion of the total spectrum and other methods are used to increase this proportion to improve the precision for trace element analysis.

A number of techniques are commonly used in EDXRF to improve analysis at trace levels, including primary filtration, secondary targets, polarisation and, crystal diffraction.

In the case of secondary targets, primary radiation from the X-ray tube is used to fluoresce a secondary target formed from a pure material, such as a metal. The secondary radiation emitted by the pure material is then used to excite the sample.

Because the secondary target is formed from a pure material, the emitted secondary radiation has a very specific profile which is characteristic of the target material and which is generally different from the anode material used in the X-ray tube. Furthermore, much of the primary radiation, including the background continuum, is absorbed by the secondary target. Accordingly, when compared with the primary radiation from the tube (which has continuum and characteristic radiation determined by the tube potential and the tube anode material), the secondary radiation is dominated by essentially monochromatic emission characteristic of the secondary target that is much more intense than the scattered continuum and characteristic radiation from the X-ray tube.

However, the secondary radiation usually has a much lower intensity, making secondary target excitation much less efficient than direct excitation. Furthermore, the range of elements efficiently excited by the monochromatic emission from the secondary target is limited. It is therefore usual to have a number of different secondary targets for general multielement analysis.

When the characteristic radiation from the secondary target strikes the sample it can also be scattered into the X-ray detector and this scattered radiation has to be processed by the detection system. This restricts the maximum count rate that can be achieved from the elements of interest. Furthermore, scattered radiation which has lost some energy compared to the incident radiation ("inelastic scatter") contributes to the background on the low energy side of the scattered characteristic peak. These effects degrade the lower limit of detection for certain elements in light matrices.

The use of polarisation in X-ray spectrometry is described in detail by R. W. Ryon, J. D. Zahrt in "Polarised Beam X-ray Fluorescence", Handbook of X-ray Spectrometry Ed1, Chapter 10 and is the subject of U.S. Pat. No. 3,944,822. In this scenario X-rays become plane polarised after they are scattered through 90°. The two most common methods used in EDXRF to polarise the beam from the X-ray tube are Barkla scatter from a low atomic number material, and Bragg diffraction from a crystalline substance.

When the three beams from X-ray tube to polariser, polariser to sample and sample to detector are positioned in a Cartesian (xyz) geometry the polarised X-ray photons scattered from the polariser have a low probability of scattering at a right angle from the sample into the detector. However, characteristic fluorescence radiation from elements in the sample is not polarised and therefore will be detected.

In theory, this is a very effective method of eliminating background radiation. However the tight collimation required to constrain the 90° beams can result in a very low intensity of radiation reaching the detector making it difficult to obtain precise measurements.

The degree of polarisation and intensity are inversely related. Accordingly, in practice, a compromise is usually necessary and complete polarisation is sacrificed by opening up the collimation to give a reasonable count rate but still a very significant reduction in scattered radiation.

The document entitled "The comparison of three excitation modes in EDXRF", Adv. X-ray Anal. 35 (1992), 1001–1007 by Kanngiesser et al compares different modes of excitation in EDXRF. One of the conclusions of this document was "the lower detection limits [for Barkla polarisation] were achieved in spite of the poorer peak-to-background ratios. The reason for this is the absence of the strong (Rayleigh and Compton) scattering peaks in the case of secondary excitation, which aggravate the electronics without contributing to the analysis".

Barkla polarisers must have a low atomic number and high density to give greatest scattering efficiency and materials such as $B_4C$ and C (amorphous graphite) are commonly used for low energy X-rays, whilst $Al_2O_3$ is used for higher energies. The scattered radiation is polychromatic and therefore suitable for multielement applications.

The choice of Bragg polarisers is more restricted because of the requirement to diffract X-rays at a Bragg angle ($2\theta$)

of 90°. One of the most promising materials is highly oriented pyrolytic graphite (HOPG) which has an exceptionally high integral reflectivity. HOPG is particularly useful in combination with X-ray tube anode materials such at Rhodium (Rh) and Palladium (Pd) which are widely used in EDXRF. The L$\alpha$ lines produced from these particular anode materials diffract at Bragg angles very close to 90° i.e. Rh L$\alpha$ (2.696keV) at 86.5° and Pd L$\alpha$ (2.838 keV) at 81.20. The polarised radiation diffracted from HOPG is essentially a series of monochromatic lines at multiples of the predominant first order energy. The higher order lines are weaker but extend the energy range for excitation. HOPG also acts as Barkla scatterer which increases its polarising properties. High energy Barkla scatter can be further enhanced by fixing the HOPG onto a pure Al or $Al_2O_3$ substrate.

Another very important property of HOPG is that it can be formed into various shapes using special techniques described by I. G. Grigorieva and A. A. Antonov in "HOPG as a powerful X-ray Optic", Proceedings of European Conference on EDXRS-98, 115–119 (1998). Intensities can be increased by up to an order of magnitude by using a Johann semi-focusing geometry with singly bent (cylindrical) or doubly bent (spherical or toroidal) HOPG.

It has also been proposed to provide systems which allow different forms of excitation to be achieved. Thus, for example, the Cartesian geometry needed for polarisation also lends itself to secondary target excitation (but not vice versa). Accordingly, commercial instruments have been provided in which a number of secondary and polarisation targets are available for sequential measurements. In these instruments the different targets can be moved and brought into alignment with the X-ray tube beam.

Other instruments combine direct (and filtered) excitation with secondary targets. In this technique, which is described in U.S. Pat. No. 3,919,548, the X-ray tube is rotated between two positions with the beam directed either at the sample or onto a secondary target.

A later U.S. Pat. No. 6,041,095 describes an alternative system to allow direct and secondary target excitation. This technique uses the fact that the beam from a conventional X-ray tube is broad enough to be directed at both a sample and a secondary target without having to move the tube. The mode of excitation is selected by a simple two position aperture in front of the tube. However, the configuration proposed in this patent is limited to use for direct and secondary target excitation and would not function for polarisation.

SUMMARY OF THE INVENTION

In accordance with the present invention, we provide apparatus for analysing a sample, the apparatus comprising:
a. A radiation source for generating a radiation beam;
b. A sample holder for holding the sample in use;
c. A polariser for polarising the radiation beam;
d. A radiation beam selector for selectively exposing the sample to either the radiation beam or the polarised radiation beam; and,
e. A detector for detecting radiation emitted by the sample.

Accordingly the present invention provides apparatus for analysing a sample in which direct (and filtered) excitation is combined with a polariser in a single analysis head.

This is achieved by using a polariser to generate a polarised radiation beam from the radiation source. A radiation beam selector is then used to selectively expose the sample either to the direct radiation beam or to the polarised radiation beam.

The development of a single analysis head has resulted from a study on the limits of detection in light matrices using various modes of excitation including secondary target excitation. The study concluded that, for the same power level in the X-ray tube, polarisation using doubly bent HOPG is best for multielement analysis in the range from sodium (Na) to sulphur (S), whereas direct excitation is favoured for multielement analysis at higher atomic numbers.

Preferably the radiation beam selector defines first and second beam paths, the first beam path directing the radiation towards the sample holder so as to expose the sample to the radiation beam, the second beam path directing the radiation beam towards the polariser so as to expose the sample to the polarised radiation beam.

The selector will usually comprise of an aperture positioned adjacent the radiation source, the aperture being movable between first and second positions to define the first and second beam paths respectively. As an alternative, the aperture could be positioned adjacent the sample holder to selectively block either the direct radiation beam or the polarised radiation beam.

Typically, the aperture is a simple linear sliding aperture. Alternatively the aperture may be formed from a rotating aperture device, or any suitable method of blocking one beam and allowing another beam to pass, such as a shutter system.

In the case in which an aperture is used, the radiation source is preferably adapted to generate a wide angle radiation beam incident on both the first and second aperture positions. This allows both the first and second aperture positions to be exposed without the radiation source having to be moved.

As an alternative however, the radiation beam selector could comprise the radiation source movable between first and second positions to generate a radiation beam along a respective one of the first or second beam paths.

The radiation source generates the radiation beam along a beam axis. In the case in which a stationary radiation source is used, the sample holder and the polariser are typically positioned within at least 30% of the beam axis. This ensures that the wide angle radiation beam can be incident on both the sample holder and the polariser.

In the case where the apparatus is adapted to perform X-ray analysis, the radiation source is an X-ray tube and in particular, usually an end window X-ray tube with the anode close to the exit window. This ensures that a wide angle radiation beam is produced.

Similarly, the detector is usually a Lithium drifted Silicon Si(Li) detector. Although any suitable detector such as Si, Ge, CdZnTe, $HgI_2$, or a gas filled proportional counter can be used.

The polariser usually comprises an HOPG polariser designed to diffract the radiation beam towards the sample holder, thereby exposing the sample to polarised radiation. In order to achieve this, the direction from radiation source to the polariser, the direction from polariser to the sample, and the direction from sample to detector are typically orthogonal to each other to minimise the amount of scattered radiation reaching the detector relative to the fluoresced radiation from the sample.

Furthermore, the polariser is advantageously arranged in a Johann semi-focusing geometry to enhance the diffracted intensity.

The radiation source usually further comprises one or more filters for selectively filtering the radiation forming the radiation beam although this is not essential to the operation of the invention.

BRIEF DESCRIPTION OF THE DRAWINGS

Examples of the present invention will now be described with reference to the accompanying drawings, in which.

DETAILED DESCRIPTION OF EMBODIMENT

Figure 1:
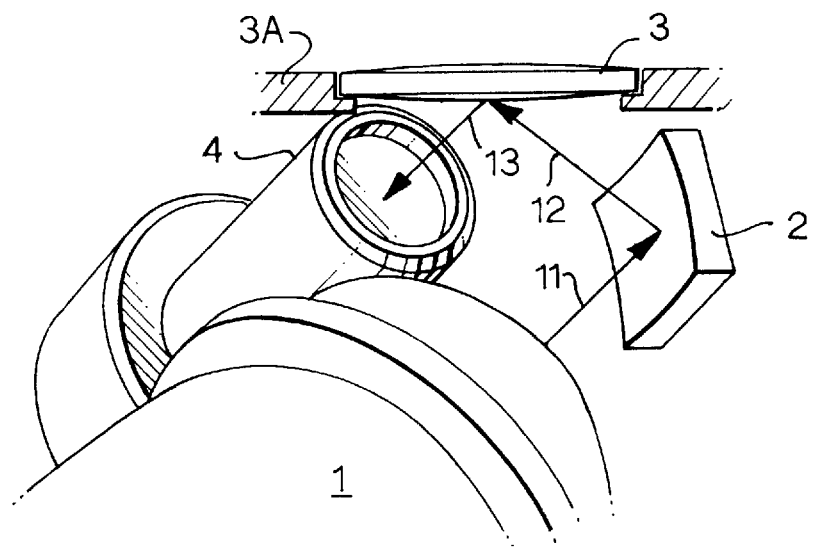
FIG. 1 is a three-dimensional schematic diagram showing the geometry of apparatus for analysing a sample according to a first example of the present invention.
Figure 2:
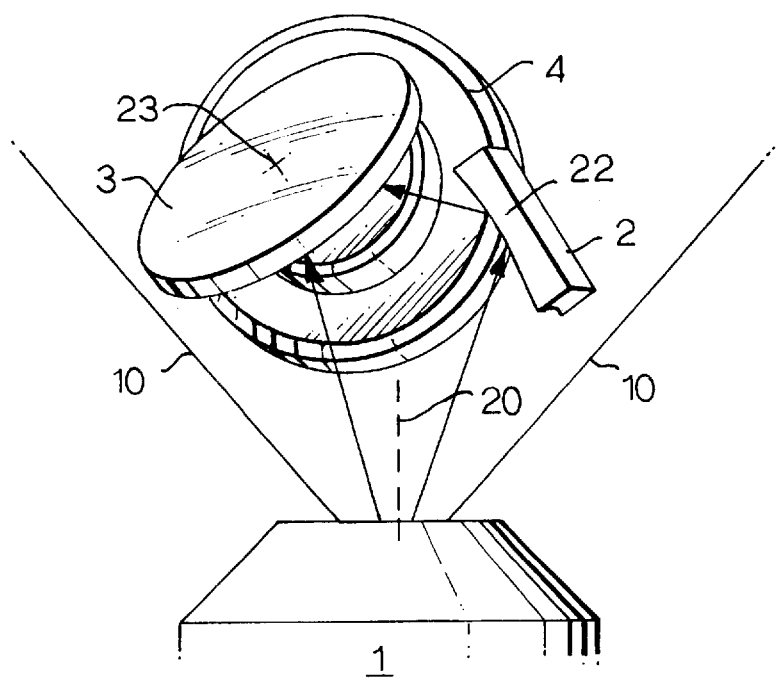
FIG. 2 is a three-dimensional schematic diagram of an alternative view of the geometry of the apparatus of FIG. 1 with the sample holder omitted.
Figure 3:
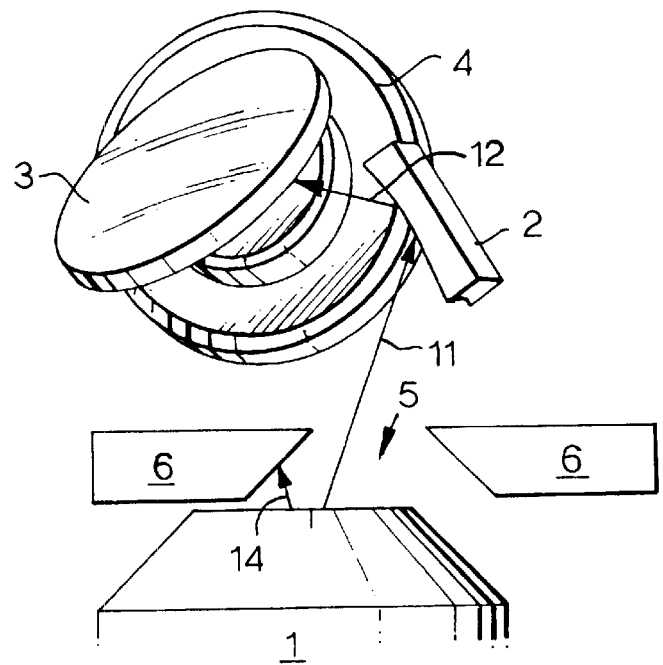
FIGS. 3 and 4 are three-dimensional schematic diagrams, with the sample holder omitted, showing the use of the beam selector to select either the polarisation mode or the direct mode of excitation in the apparatus of FIG. 1; and, FIG. 5 is a schematic diagram showing the geometry of apparatus for analysing a sample according to a second example of the present invention.
Figure 4:
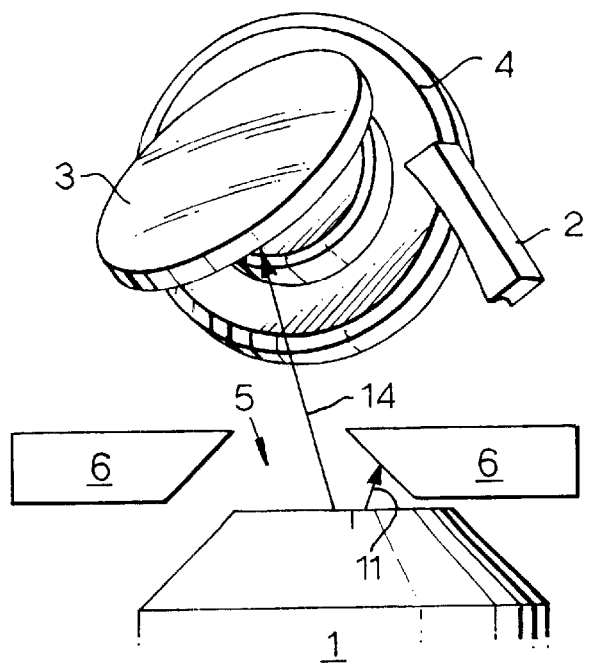

An example of apparatus according to the present invention is shown in FIGS. 1 to 4. The apparatus comprises an X-ray tube 1, a polariser 2, a sample 3 and a Si(Li) detector 4. The sample 3 is held in position by a sample holder 3A. Also shown in FIGS. 3 and 4 is an aperture 5 formed from a sliding shutter 6.

The X-ray tube emits a beam of primary radiation shown generally at 10.

Accordingly, the X-ray tube 1 emits the radiation beam 10 over a wide angle as shown. This property is typical of an end window X-ray tube with an anode close to the exit window. In this example, the X-ray tube is a VF50J from Varian. The VF50J has a maximum cone angle of 38° but the beam will only be used out to 30° as shown at 10. At this angle the intensity, in the worst case (for low energies), is still 90% of that at the centre of the beam. The use of the VF50J is advantageous as the spot size on the anode is small (1 mm square). This makes it particularly suitable for use with a bent HOPG crystal which is used as the polariser 2 in a Johann semi-focusing geometry. In this example, the chosen target material is Palladium Pd.

FIGS. 1 to 4 show the geometry of the apparatus in 3-D. FIG. 1 is a general overview showing the main components, as well as centre lines for the radiation beams for the polarisation mode of operation. In this case, the centre line of the primary radiation beam from X-ray tube 1 to polariser 2 is shown at 11. The secondary beam from the polariser 2 to the sample 3 is shown at 12, whilst the emitted beam from the sample 3 to the Si(Li) detector 4 is shown at 13.

The polariser 2 is drawn with a doubly curved surface which would be the case for HOPG, although this will not necessarily be the case for other polarisers.

FIG. 2 shows the configuration from another angle and shows how the full cone of radiation 10 from the X-ray tube extends beyond both the sample 3 for direct excitation, and the polariser 2 for polarised excitation. The X-ray tube 1 is positioned with a central axis 20 laying approximately mid-way between a centre 23 of the sample 3 and a centre 22 of the polariser 2. The angles from X-ray tube axis to centres 23,22 of sample 3 and polariser 2 are each about 15° and approximately 30° to the extremes of both.

FIGS. 3 and 4 show a beam selector 5,6 in the form of the movable aperture 5 positioned in front of the X-ray tube 1 so as to enable the required modes of excitation to be selected.

As will be appreciated by the skilled person, when the aperture 5 is in a first position shown in FIG. 3, the radiation beam 10 from the X-ray tube 1 cannot directly impinge on the sample 3 as shown at 14. However, as shown by the centre line 11 the radiation beam does expose the polariser 2.

The polariser 2 is located so that the plane containing the beam which strikes the polariser 2 and the polarised beam which strikes the sample 3 is perpendicular to the direction from the sample 3 to the detector 4. This prevents scatter of the polarised radiation from the sample surface. Accordingly, the polarised beam of radiation impinges on the sample resulting in the desired polarisation excitation.

Similarly, FIG. 4 shows a second aperture position in which the aperture 5 allows the radiation beam 10 to expose the sample 3 directly as shown by the centre line 14. In this case, the portion of the radiation beam directed towards the polariser 2 (shown at 11) is blocked as shown.

The beam selector is shown as a sliding aperture but could, for example, be a rotating device. A third position, not shown, could act as a radiation safety shutter to completely block off the primary beam.

The diagrams do not show the fixed collimators that are needed to constrain the beams to the polarising geometry. Also not shown is a thin moveable wheel or slide which can be positioned directly in front of the X-ray tube window containing a series of primary filters. These filters are typically thin metal foils and are normally included in all EDXRF systems to improve the quality of the primary X-rays, as will be appreciated by a person skilled in the art.

The diagrams show a single fixed polariser however it would be feasible to have more than one mounted on a moveable slide or wheel which could automatically be selected to suit a particular application.

Figure 5:
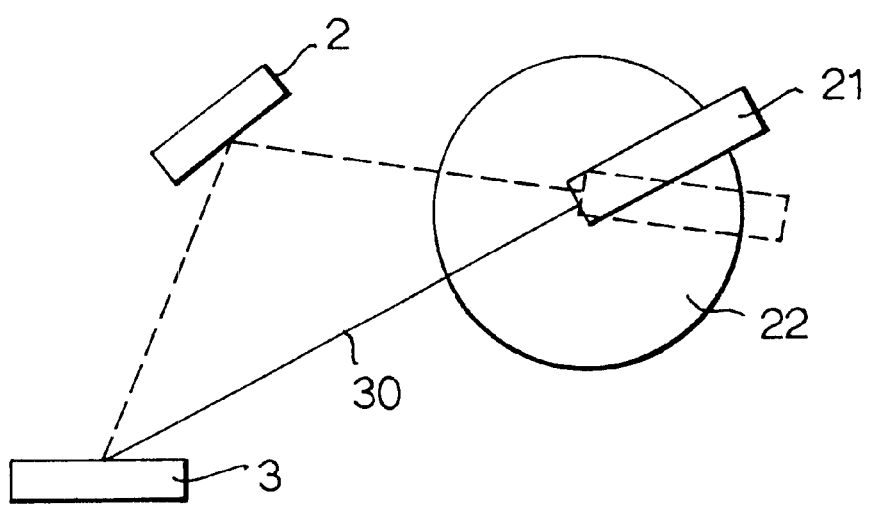

Apparatus according to a second example of the present invention is shown in FIG. 5. In this example, similar reference numerals are used to refer to similar components contained in FIGS. 1 to 4. Furthermore, this is a 2-D representation, and accordingly the detector 4 is not shown as this lies outside the plane of the drawing, as will be evident for example from the geometry of the first example shown in FIG. 2.

In this example, an X-ray tube 21 is fitted to a rotatable mounting 22, as shown. The X-ray tube 21 emits a narrower angle beam of radiation shown at 30 than in the previous example. The X-ray tube 21 is movable between at least first and second positions. In FIG. 5 the first position of the X-ray tube 21 is shown in continuous lines, with the second position being shown in dotted lines.

Accordingly, as shown in the first position the radiation beam 30 impinges on the sample 3 which is held in place by a sample holder (not shown). This position corresponds to the position of the radiation beam 14 in FIG. 4.

In contrast to this, in the second position, the radiation beam 30 from the X-ray tube 21 impinges on a polaripolariser 2. This position corresponds to the position of the radiation beam 11 in FIG. 3. Accordingly, by rotating the X-ray tube 21 between the first and second positions, this allows direct and polarised modes of excitation to be selected.

I claim:

1. Apparatus for analysing a sample, the apparatus comprising:
   a. A radiation source for generating a radiation beam;
   b. A sample holder for holding the sample in use;
   c. A polariser for polarising the radiation beam;
   d. A radiation beam selector for selectively exposing the sample to either the radiation beam or the polarised radiation beam; and, e. A detector for detecting radiation emitted by the sample.

2. Apparatus according to claim 1, wherein the radiation beam selector defines first and second beam paths, the first beam path directing the radiation beam toward the sample holder so as to expose the sample to the radiation beam, the second beam path directing the radiation beam towards the polariser so as to expose the sample to the polarised radiation beam.

3. Apparatus according to claim 2, wherein the radiation beam selector comprises an aperture positioned adjacent the radiation source, the aperture being movable between first and second positions to define the first and second beam paths respectively.

4. Apparatus according to claim 3, wherein the radiation source is adapted to generate a wide angle radiation beam incident on both the first and second aperture positions.

5. Apparatus according to claim 4, wherein the radiation source generates the radiation beam along a beam axis, the sample holder and the polariser being positioned within at least 30° of the beam axis.

6. Apparatus according to claim 1, wherein the radiation beam selector comprises the radiation source movable between first and second positions to generate a radiation beam along a respective one of the first or second beam paths.

7. Apparatus according to claim 1, wherein the apparatus is adapted to perform X-ray analysis, the radiation source comprising an X-ray tube.

8. Apparatus according to claim 5, wherein the detector is a Si(Li) detector.

9. Apparatus according to claim 1, wherein the polariser comprises an HOPG polariser adapted to diffract the radiation beam toward the sample holder, thereby exposing the sample to polarised radiation.

10. Apparatus according to claim 1, the radiation source further comprising one or more filters for selectively filtering the radiation forming the radiation beam.

* * * * *